(12) United States Patent
Orfao et al.

(10) Patent No.: US 6,667,149 B1
(45) Date of Patent: Dec. 23, 2003

(54) PROCEDURE FOR THE ANALYSIS OF THE FUNCTIONAL ACTIVATION OF LEUKOCYTES, PLATELETS AND OTHER CELLS, INDUCED IN VIVO OR IN VITRO, BASED ON THE STABILIZATION OF CYTOPLASMIC MEMBRANE PROTEINS AND ITS DETECTION USING QUANTITATIVE CYTOMETRIC METHODS IN THE ABSENCE OF ADDITIONAL SAMPLE MANIPULATION

(75) Inventors: Alberto Orfao, Salamanca (ES); Atanasio Pandiella, Salamanca (ES)

(73) Assignee: Universidad De Salamanca, Patio Escuelas Menores (ES)

( * ) Notice: Subject to any disclaimer, the term of this patent is extended or adjusted under 35 U.S.C. 154(b) by 0 days.

(21) Appl. No.: 09/583,172

(22) Filed: May 30, 2000

(30) Foreign Application Priority Data

May 31, 1999 (ES) .................................................. 9901181

(51) Int. Cl.$^7$ ........................ G01N 33/53; G01N 33/567; A01K 38/40
(52) U.S. Cl. ................................ 435/2; 435/3; 435/7.2; 435/7.71; 435/23; 435/69.2; 435/40.5; 436/64; 436/63; 436/517; 436/519; 436/548; 436/172
(58) Field of Search ......................... 435/1.1, 2, 3, 7.2, 435/7.23, 7.24, 7.71, 23, 40.5, 40.51, 40.52, 69.2, 69.3, 69.5, 69.51, 69.52, 173.4, 173.7, 173.8, 184, 188; 436/517, 519, 537, 546, 548, 63, 64, 172, 813

(56) References Cited

U.S. PATENT DOCUMENTS 5,627,040 A * 5/1997 Bierre et al. ................ 435/7.24
5,858,357 A * 1/1999 Trnka et al. ............. 424/94.64
5,981,180 A * 11/1999 Chandler et al. .............. 435/6
6,068,984 A * 5/2000 Tedder et al. ............... 435/7.24

OTHER PUBLICATIONS

Kahan et al., Detecting Intracellular Cytokines in Activated Monocytes, Becton Dickinson : Application Note 2, pp. 1–11 (1997.*
Becton Dickinson Systems, Detection of Intracellular Cytokines in Activated Lymphocytes, Becton Dickinson : Application Note 1, pp. 1–12 (1997).*
Suni et al., Detection of antigen–specific T cell cytokine expression in whole blood by flow cytometry, Journal of Immunological Methods 212: 89–98 (1998).*
Willman et al., Peripheral Blood Dendritic Cells Revealed by Flow Cytometry, Becton Dickinson : Applicaiton Note 3, pp. 1–12 (1998).*
De Saint–Vis et al., The cytokine profile expressed by human dendritic cells is dependent on cell subtype and mode of activation The Journal of Immunology 160: 1666–1676 (1998).*
Prussin, Cytokine flow cytometry: assessing cytokine production at the single cell level, Clinical Immunology 6: 85–91 (Jun. 1996).*
Caestecker et al., The detection of intracytoplasmic interleukin and tumor necrosis factor expression in human monocytes using two colour immunofluorescence flow cytometry, Journal of Immunological Methods, 154: 11–20 (1992).*
Debets, et al., Cross–Linking of Both FC–GAMMA–RI and FC–GAMMA–RII Induces Secretion of Tumor Necrosis Factor by Human Monocytes, Requiring High Affinity FC–FC–GAMMA–R Interactions, Journal of Immunology, vol. 144, No. 4, (1990) pp. 1304–1310—XP002200740.
Remold–O'Donnell et al., Two Proteolytic Pathways for Down–Reulation of the Barrier Molecular CD43 of Human Neutrophlis, Journal of Immunology, vol. 152, No. 7 (1994) pp. 3596–3599—XP002200739.
Remold–O'Donnell et al., Downregulation of neutrophil CD43 by opsonized zymosan—XP002200741—Abstract.
The cytoplasmic tail of the T cell receptor zeta chain is required for signaling via CD26—Database accession No. PREV199598139850—XP002200742—Abstract.

* cited by examiner

*Primary Examiner*—Long V. Le
*Assistant Examiner*—Jacob Cheu
(74) *Attorney, Agent, or Firm*—Blank Rome LLP

(57) ABSTRACT

Procedure for the study of the functional activation of leukocytes, platelets and other cells, produced in vivo or induced in vitro, based on the stabilization of cytoplasmic membrane proteins and its detection using quantitative cytometric methods in the absence of any further manipulation of the sample. The procedure includes the sequential incubation of the sample with: 1) either one or a mixture of more than one protease specific inhibitors and, 2) a combination of several fluorochrome-conjugated monoclonal antibodies; to analyze the expression of surface proteins using immunofluorescence methods and quantitative cytometry.

8 Claims, No Drawings

PROCEDURE FOR THE ANALYSIS OF THE FUNCTIONAL ACTIVATION OF LEUKOCYTES, PLATELETS AND OTHER CELLS, INDUCED IN VIVO OR IN VITRO, BASED ON THE STABILIZATION OF CYTOPLASMIC MEMBRANE PROTEINS AND ITS DETECTION USING QUANTITATIVE CYTOMETRIC METHODS IN THE ABSENCE OF ADDITIONAL SAMPLE MANIPULATION

BACKGROUND OF THE INVENTION

The invention is mainly related, although not exclusively, with a procedure for a rapid, cost-effective, sensitive and specific quantitation of the accumulative expression of proteins which are usually transiently expressed in the cytoplasmic membrane and reflect a functionally activated specific state in response to a stimuli which has acted in vivo or has been administered in vitro, through the use of compounds able of selectively inhibiting the cleavage and secretion of cytoplasmic membrane proteins to the extracellular media without affecting the functionality of the cell. The invention can be used both with normal and pathological cells present in homogeneous or heterogeneous cell samples for any purpose which requires either the analysis of the expression of membrane proteins associated with the functional activation of the cell or the stabilization of membrane proteins, particularly for diagnostic, prognostic and treatment monitoring purposes.

At present it is well known that any functional process which takes place at the single cell level is reflected, among other manifestations, by the existence of changes in the expression of different cell proteins. Among these modifications, particularly relevant are those changes in the expression of membrane proteins, where they act as receptors and ligands for the transmission of cell-to-cell and cell-extracellular protein signals. Frequently, once a protein has played its role in the cell membrane or, sometimes immediately after a protein has reach ed the cytoplasmic membrane of the cells that have produced it, these proteins are cleaved and leare the cell membrane into the extracellular media through the activity of proteases and especially membrane proteases which specifically act on the cells where they are expressed. Thus, the expression of these membrane proteins frequently occurs in a transient way for variable periods of time, their expression depending not only on their production rate but also on the speed at which they are cleaved from the cell membrane and secreted to the extracellular media.

For a long time it is well known that the potential relevance of the measurement of these membrane proteins as functional activation markers in different cell types, is high. Nevertheless, since their expression on the cell surface is transient, the analysis of their levels on the cytoplasmic membrane has not been routinely used. Alternatively, measurements of these proteins have been made at three different levels: 1) quantitation of the protein secreted to the extracellular media (soluble protein), 2) qualitative evaluation (presence/absence) of the expression of the protein on the cytoplasmic membrane and, 3) the combined assessment of both forms of the protein. However, such determinations do not provide a specific and/or sensitive information about the production of these proteins in individual cells. Because of this, more recently, methods have been developed which allow the quantitation of the overall production of specific proteins for a specific period of time at the single cell level. For that purpose chemical compounds which induce a blockade of the intracellular transport of secretion vesicles such as brefeldin A or monensin have been used to induce the intracellular accumulation of proteins produced in response to a specific stimuli that can occur in vivo or be administered in vitro. The use, in this later group of techniques, of agents that block the transport and extracellular secretion of proteins in a non-specific way at the cytoplasm level has three major disadvantages: 1) their use can be associated with unwanted changes in other cell functions, 2) the use of this methodology would not block the release outside the cell of those molecules of the protein which had reached the cell membrane prior to the administration of the blocking agent and, 3) for the detection of the proteins of interest at the single cell level the use of fixation and permeabilization solutions is required, which decreases the sensitivity of the method for the detection of the protein and represent a limitation for its objective quantitative analysis.

SUMMARY OF THE INVENTION

Up to now, no procedure has been described which, with minimum sample manipulation, allows the functional analysis of activation of individual cells, based on the stabilization and both the quantitative and accumulative analysis of the levels of membrane proteins whose expression on the cell surface is usually transient.

Therefore a goal of this invention consists on proposing a solution for the study of the functional activation of leukocytes, platelets and other cells either produced in vivo or induced in vitro, based on the stabilization of proteins from the cytoplasmic membrane and their detection in unmanipulated samples using quantitative cytometric techniques.

In a similar way, another aim of this invention consists of knowing the kinetics of the activity of proteases which participate in processing, cutting and releasing outside the cell membrane, proteins which are associated to functional activation processes from leukocytes, platelets and other cells that can be induced either in vivo or in vitro.

More specifically and in agreement with what has been described above, the procedure of this invention for the study of the functional activation of leukocytes, platelets and other cells, produced either in vivo or induced in vitro, is based on the stabilization on the cytoplasmic membrane of proteins which have a transient expression on the cell surface and their detection using quantitative cytometric techniques, in the absence of additional sample manipulation, being comprised of the steps of:

1) sequential incubation of the sample with an inhibitor (or a combination of inhibitors) specific of the protease or proteases that process these membrane proteins and a mixture of antibodies directly conjugate to fluorochromes.
2) Detection, using quantitative cytometric techniques (for instance, flow cytometry), in a direct way and in the absence of additional sample manipulation, of the expression of the accumulated membrane proteins through the measurement of the fluorochromes directly bound to the cells through the conjugated antibodies.
3) Analysis of the results obtained using a multiparametric analytical approach for the identification of the subsets of cells of interest and to identify within them, those that express the stabilized membrane proteins. quantifying their expression in an objective way based on the fluorescence intensity detected.

After obtaining the sample in the presence of the protease inhibitors mentioned earlier, the use of procedures for the in vitro stimulation of the functional activation of cells, staining with antibodies, the adjustment and calibration of the cytometer are performed in accordance to widely described methods which are recommended for the quantitative analysis of protein expression on the cell membrane. For the selection of the specific cell subsets present in the sample in which it is desired to perform the determination, antibodies will be used that specifically identify those cells and that allow their discrimination from other subtypes of cells present in the sample, therefore avoiding additional sample manipulation.

For the analysis of the results as well as for the accurate and precise quantitation of the expression of each protein of interest, different software programs can be used from which the PAINT-A-GATE PRO™ software is especially useful. During the analysis, apart from the negativity/positivity for each antibody staining one or more specific cell subsets, fluorescenceintensity expressed in objective units including median, mean and dispersion values will be used.

The invention can be used both in normal and in pathologic samples from humans or animals, vegetables, bacterias and other microorganisms, obtained in vivo, stored or treated in vitro, for all the purposes in which the analysis of either the status or the capabilities of functional activation of leukocytes, platelets or other cells is required.

As it can be deduced from what has been described above, the stabilizing compounds (protease inhibitors), the antibodies and/or the fluorochromes can vary mainly depending on the type of proteins functions and/or the types of cells to study, or depending on the type of sample used. Such protease inhibitor is a monoclonal antibody, an aminoacid or aminoacid derived product or a peptide.

In addition, variations in which the number of antibodies used in combination with a fluorochrome is higher than one and those modifications of by the technique in which monoclonal antibodies conjugated with more than one fluorochrome are used, are included in this invention. A pool or more than one pool of monoclonal antibodies conjugated with the saine fluorochrome and directed to one or more different cell subpopulations can be used. Each pool of antibodies used being conjugated with a different fluorochromes.

Finally, in this invention are included those variations in which, after incubating the sample with the antibodies in the presence of stabilizing substances, these can be removed in order to explore the kinetics of action of these proteases that participate in processing, cutting, and releasing outside the cell of membrane proteins associated to the processes of functional activation of leukocytes, platelets and other cells produced in vivo or induced in vitro.

Moreover, in this invention, apart from the staining of the subpopulations of cells and the stabilized proteins under study, the measurement of other surface markers including oncoproteins and proteins related to cell cycle, apoptosis or cell activation and differentiation, can also be performed.

In order to explore such kinetics of action of the proteases involved in processing, cutting and releasing outside the cell those membrane proteins which are associated with the processes of functional activation produced in vivo or induced in vitro of leukocytes, platelets and other cells, after performing the incubation of the sample with the antibodies in the presence of the stabilizing substances, these later can be either removed or their effects reversed.

With this invention we significantly optimize the study of the functional activation of leukocytes, platelets and other cells in biological samples activated in vivo or stimulated in vitro, also allowing the analysis of the kinetics of action of membrane proteases.

It should also be considered that the possibility of stabilizing membrane proteins whose expression in the cell surface is transient or even lasting for very short periods of time provides a detailed information on the functional activation status of the cells analyzed.

The invention can be used for the identification of cells, based on the presence or absence of staining for one or several antibodies or combinations of antibodies used or based on the fluorescence intensity obtained for them.

It should be noted that according to the present invention, the incubation with the membrane protein stabilizing agent could also be performed in vivo prior to obtain the sample.

The invention will be illustrated by three examples which do not limit its area of application as follows:

DETAILED DESCRIPTION OF THE PREFERRED EMBODIMENTS

EXAMPLE 1

1.—Material and Methods

Peripheral blood (PB) was obtained in two different tubes from 10 healthy volunteers. One tube contained heparin and the second tube contained heparin and an inhibitor of the TACE metalloprotease responsible for processing and releasing tumor necrosis factor (TNF) alpha from the cytoplasmic membrane outside the cell to the extracellular media. The analysis of TNF-α expression on the cytoplasmic membrane was performed after inducing its production by T-cells and natural-killer (NK)-cells with phorbol esters (PMA) and ionomycin, using a direct immunofluorescence technique analyzed by flow cytometry.

2.—Sample Preparation

20 μL of PB were taken from each of the two tubes and placed in separate tubes which have been clearly labeled in advance. To each of these two tubes 80 μL of RPMI 1640 cell culture media supplemented with 10% foetal bovine serum and 1% glutamine were added. Afterwards 25 μL of a solution containing PMA plus ionomycin (final concentration of 25 ng/mL and 1 μg/mL, respectively) were added; after vortexing the tubes, they were incubated for 2 hours at 37° C. in a humidified atmosphere containing 5% $CO_2$. After this incubation, the sample was divided into two identical parts which were placed into two different tubes (50 μl/tube). To one of these tubes 20 gL of each of the following monoclonal antibodies conjugated with fluorochromes (fluorescein isothiocynate-FITC, phycoerythrin-PE PE/cyanin 5 PE/Cy5 and allophycianin AAPC) were added: CD3 (leu 4)-FITC/anti-TNFα-PE/CD56-PECy5/CD45-APC. The specificity and source of the monoclonal antibodies was as follows:

1) Leu-4-FITC (CD3): pan-T cell marker (Becton Dickinson, San José, Calif., USA).
2) 6401.1111-PE (anti-TNFα): identifies tumor necrosis factor (Becton Dickinson).
3) NKI-nbl-1-PECy5 (CD56): marker which identifies NK-cells and a subpopulation of T-cells (Caltag Laboratories, San Francisco, Calif., USA).
4) HI30-APC (CD45): pan-leukocyte marker (Caltag Laboratories).

To the other tube, used as isotype control, the same monoclonal antibodies were added except for the antibody against TNF-α which was replaced by ar mouse monoclonal antibody of the same isotype as the anti-TNF-α reagent (also conjugated with PE) and directed against a protein which is not expressed on cells from human PB. Both tubes were gently vortexed and incubated for 10–15 minutes at room temperature, in the darkness. Immediately after this incubation period 2 mL of the QUICKLYSIS (Cytognos, Salamanca, Spain) lysing solution was added to each tube followed by a 4–5 seconds vortex. Afterwards, cells were incubated for an additional 10 minutes period in the darkness (room temperature). After this period, the fluorescent stainings were measured in a flow cytometer.

3.—Data Adquisition and Analysis

All measurements were performed in a FACSCalibur flow cytometer (Becton Dickinson) equiped with two lasers tuned at 488 nm and 650 nm, respectively. Instrument set-up and calibration. was performed using the AUTOCOMP (Becton Dickinson) software program and CALIBRITE microbeads (Becton Dickinson). For data acquisition the CellQuest software program (Becton Dickinson) was used information being exclusively stored on CD45-positive cells. After storing the information on the fluorescent stainings performed on PB samples, information was acquired on the fluorescence of a mixture of 6 different subpopulations of microbeads, each one stained with a different well-known amount of PE molecules (QUANTIBRITE microbeads, Becton Dickinson). For their measurement the subpopulations of microheads were diluted in 2 mL of QUICLYSIS solution.

Data analysis was performed using the PAINT-A-GATE PRO (Becton Dickinson) software program using a logarithmic transformation of the sideward light scatter (SSC) parameter to obtain a better separation between the different types of CD45-positive cells present in the PB samples.

TNFα expression on the cytoplasmic membrane of each cell was specifically analyzed for T-cells ($CD45^{++}/CD3^+$) and NK-cells ($CD45^{++}/CD3^-/CD56^+$) numerical information being recorded on the percentage of surface TNFα-positive cells and the intensity of TNFα expression among the subpopulations of positive cells (mean, median and coefficient of variation) in relative fluorescence chanels (arbitrary units scaled from 0 to 10.000). In order to be able to compare the results of experiments performed either in different days or in different laboratories, the QUANTIBRITE microbeads were used as a standard to convert fluorescence intensity expressed in arbitrary units (fluoresccence channels) into the number of molecules equivalent of soluble phycoerythrin (MESF).

EXAMPLE 2

PB sample were obtained by venous puncture from 10 healthy volunteers and each sample was placed into two tubes. One tube contained heparin and the second tube contained heparin and an inhibitor of the TACE metalloprotease responsible of processing and releasing.

For processing and releasing L-selectin (CD62L) from the cytoplasmic membrane of the leukocytes to the extracellular media. Analyses of cytoplasmic membrane CD62L expression was performed using a direct immunofluorescence technique analyzed by flow cytometry.

2 ※ Sample Preparation

100 μL of PB from each tube were placed into two separate polypropie tubes which had been clearly labeled in advance. To each of these two tubes 80 μL of RPMI 1640 cell culture media supplemented with 10% fetal bovine serum and 1% glutamine were added. Afterwards 25 μL of a solution containing PMA plus ionomycin (final concentration of 25 ng/ml and 1 μg/ml, respectively) were added; after vortexing the tubes they were incubated for 2 hours at 372 C in a humidified atmosphere containing 5% $CO_2$. After this incubation the sample was divided into two identical parts which were placed into two different tubes (50 μL/tube). To one of these tubes 20 μL of each of the following monoclonal antibodies conjugated with fluorochromes (fluorescein isothiocyanate-FITC, phycoerythrin-PE, PE/cyanin 5 IPE/Cy5) were added: CD14-FITC/CD62L-PE/CD45-PECy5. The specificity and source of the monoclonal antibodies was as follows:

1.—LeuM3-FITC (CD14): monocytic marker (Becton Dickinson).

2.—Leu-8-PE (CD62L): adhesion molecule (L-selectin) expressed by leukocytes (Becton Dickinson).

3.—HI30-PECy5(CD45): pan-leukocyte marker (Caltag Laboratories).

To the other tube, used as isotype control, the same monoclonal antibodies were added except for that antibody against CD62L which was replaced by a mouse monoclonal antibody of the same isotype as the CD62L reagent (also conjugated with PE) and directed against a protein which is not expressed on cells from human PB. Both tubes were gently vortexed and incubated for 10–15 minutes at room temperature, in the darkness. Immediately after this incubation period 2 ml of the QUICKLYSIS.(Cytognos, Salamanca, Spain) lysing solution was added to each tube, followed by a 4–5 seconds vortex. Afterwards, cells were incubated for an additional 10 minutes period in the darkness (room temperature). After this period, the fluorescent stainings were measured in a flow cytometer.

3.—Data Adquisition and Analysis

All measurements were performed in a FACSCalibur flow cytometer (Becton Dickinson) equipped with two lasers tuned at 488 nm and 650 nm, respectively. Instrument set-up and calibration were performed using the AUTOCOMP (Becton Dickinson) software program and CALIBRITE microbeads, (Becton Dickinson). For data acquisition the CellQuest software program (Becton Dickinson) was used, information being exclusively stored on CD45-positive cells. After storing the information on the fluorescent stainings performed on PB samples, information was acquired on the fluorescence of mixture of 6 different subpopulations of microbeads! each one stained with a different well-known amount of PE molecules (QUANTIBRITE microbeads, Becton Dickinson). For their measurement the subpopulations of microbeads were diluted in 2 mL of QUICKLYSIS solution.

Data analysis was performed using the PAINT-A-GATE PRO (Becton Dickinson) software program using a logarithmic transformation of the sideward light scatter (SSC) parameter to obtain a better separation between the different types of CD45-positive cells present in the PB samples.

CD62L expression on the cytoplasmic membrane of each cel-1 was specifically analyzed for neutrophils ($CD45^+$ with high SSC) basophils ($CD45^+$ with low SSC), monocytes ($CD45^{++}$, $CD14^+$ with intermediate SSC) and lymphocytes ($CD45^{++}$ with low SSC) numerical information being recorded on the percentage of surface CD62L-positive cells and the intensity of CD62L expression among the subpopulations of positive cells (mean, median and coefficient of variation) in relative fluorescence chanels (arbitrary uni-ts scaled from 0 to 10.000). In order to compare the results of experiments performed either in different days or -in, different laboratories, the QUANTIBRITE microbeads were used as a standard to convert fluorescence intensity expressed in arbitrary units (fluorescence channels) into the number of molecules equivalent of soluble phycoerythrin (MESF).

EXAMPLE 3

1.—Material and Methods

Peripheral blood (PB) was obtained in two different tubes, from 6 healthy volunteers. one tube contained heparin and the second tube contained heparin and an inhibitor of the TACE metal loprotease responsible of processing and releasing tumor necrosis factor (TNF) alpha from the cytoplasmic membrane outside the cell to the extracellular media. The analysis of TNF-α expression on the cytoplasmic membrane was performed after inducing its production by monocytes and dendritic cells with lipopolysaccarhyde (LPS) and y-interferon (y-IFN) using a direct immnuofluorescence technique analyzed by flow cytometry.

2.—Sample Preparation

20 μL of PB were taken from each of the two tubes and placed in separated tubes which had been clearly labeled in advance. To each of these two tubes 80 μL of RPMI 1640 cell culture media supplemented with 10% fetal bovine serum and 1% glutamine were added. Afterwards to each tube 10 μL of a solution containing LPS (final concentration of 10 ng/ml) were added; after gently vortexing the tubes were incubated for 4 hours at 37° C. in a humidified atmosphere with 5% $CO_2$. After this incubation, the sample was divided into two identical parts which were placed into two different tubes (50 μL/tube). To one of these tubes, 20 μL of each of the following monoclonal antibodies conjugated with fluorochromes (fluorescein isothiocycnate-FITC phycoerythrin-PE peridin chlorophyll protein-PerCP and APC) were added CD3-CD19-CD56-CD14-FITC anti-TNFoc-PE/HLADR-PerCP/CD45-APC. The specificity and source of the monoclonal antibodies was as follows:
1.—Leu 4-FITC (CD3): pan-T-cell marker (Becton Dickinson)
2.—C5.9-FITC (CD56): neural-adhesion molecule present in NK-cells and a subpopulation of T-cells (Imico, Madrid, Spain).
3.—Leu 12-FITC (CD19): pan-B-cell marker (Becton Dickinson)
4.—Leu M3-FITC (CD14): marker present on mature monocytes (Becton Dickinson)
5.—6401.1111-PE (anti-TNFα): identifies tumor necrosis-factor α (Becton Dickinson)
6.—L243-PerCP (HLADR): marker present on antigen presenting cells; subtype of HLA class II molecule (Becton Dickinson)
7.—HI30-APC (CD45): pan-leukocyte marker (Caltag Laboratories)

To the other tube, used as isotype control, the same monoclonal antibodies were added except for that antibody against TNF-α which was replaced by a mouse monoclonal antibody of the same isotype as the anti-TNF-α reagent (also conjugated with PE) and directed against a protein which is not expressed on cells from human PB. Both tubes were gently vortexed and incubated for 10–15 minutes at room temperature, in the darkness. Immediately after this incubation period 2 mL of the QUICKLYSIS lysing solution was added to each tube, 0,5 ml of phosphate buffered saline (PBS) were added to each tube and the tubes were vortexed for 4–5 seconds. Afterwards, measurement of the fluorescent stainings were performed in a flow cytometer.

3.—Data Acquisition and Analysis

All measurements were performed in a FACSCalibur flow cytometer (Becton Dickinson) equipped with two lasers tuned at 488 nm and 650 nm, respectively. Instrument set-up and calibration was performed using the AUTOCOMP (Becton Dickinson) software program and CALIBRITE microbeads (Becton Dickinson). For data acquisition the CellQuest software program (Becton Dickinson) was used, information being exclusively stored on D45-positive cells. After storing the information on the fluorescent stainings performed on PB samples, information was acquired on the fluorescence of a mixture of 6 different subpopulations of microbeads, each one stained with a different well-known amount of PE molecules (QUICKCAL mictobeads. Flow Cytometry Standards Corporation, San Juan, Puerto Rico). For their measurement the subpopulations of microheads were diluted in 0.5 ml of PBS solution.

Data analysis was performed using the PAINT-A-GATE PRO (Becton Dickinson) software program using a logarithmic transformation of the sideward light scatter (SSC) parameter to obtain a better separation between the different types of CD45-positive cells present in the PB samples.

TNFα expression on the cytoplasmic membrane of each cell was analyzed specifically for dendritic cells ($CD45^+$/$CD3^-$/$CD19^-$/$CD14^-$/$CD56^-$/$HLADR^+$) and monocytes ($CD45^+$/$CD14^+$) numerical information being recorded on the percentage of surface TNFα-positive cells and the intensity of TNFα expression among the subpopulations of positive cells (mean, median and coefficient of variation) in relative fluorescence chanels (arbitrary units scaled from 0 to 10.000). In order to be able to compare the results of experiments performed either in different days or in different laboratories, the QUICKCAL microbeads (Flow Cytometry Standards Corporation) were used as a standard to convert fluorescence intensity expressed in arbitrary units (fluorescence channels) into the number of molecules equivalent of soluble phycoerythrin (MESF).

Although only preferred embodiments are specifically illustrated and described herein, it will be appreciated that many modifications and variations of the present invention are possible in light of the above teachings and within the purview of the appended claims without department from the spirit and intended scope of the invention.

What is claimed is:

1. A procedure for the analysis of functional activation of leukocytes and platelets produced in vivo or induced in vitro, based on i) specific stabilization of cytoplasmic membrane proteins, said proteins being expressed on the surface of said leukocytes and platelets as a consequence of said functional activation, and are rapidly cleaved from the cytoplasmic membrane, by specific cytoplasmic membrane proteases expressed by the same cell through the inhibition of said membrane proteases, ii) identification of subpopulations of said leukocytes and platelets and iii) detection of said specifically stabilized cytoplasmic membrane proteins through quantitative cytometric techniques without manipulation of cells, comprising the steps of:

(a) sequentially incubating a sample containing subpopulations of leukocytes or platelets by using an inhibitor specific for a membrane protease and a plurality of different monoclonal antibodies each conjugated with a different fluorochrome, which include: i) at least one fluorochrome-labeled monoclonal antibody specific for a stabilized cytoplasmic membrane protein; and ii) at least a second monoclonal antibody conjugated to a different fluorochrome, specific for the identification of a non-stabilized cytoplasmic membrane protein, which binds and identifies a non-stabilized cytoplasmic membrane protein whose pattern of expression is specific for a subpopulation leukocytes or platelets from the sample;

(b) measuring by quantitative cytometry the fluorescence emissions of the fluorochromes conjugated with: i) each of the monoclonal antibodies bound to a stabilized membrane protein and ii) each of the monoclonal antibodies bound to a non-stabilized cytoplasmic membrane protein whose pattern of expression is specific for a subpopulation of leukocytes and platelets from the sample, as defined in step (a); and (c) analyzing the measurements obtained in step (b), by i) identifying each subpopulation of leukocytes and platelets present in the sample based on the fluorescence emissions of the fluorochromes conjugated with the monoclonal antibodies specific for non-stabilized-cytoplasmic membrane proteins whose pattern of expression is also specific for a given subpopulation of leukocytes and platelets and ii) determining the levels of expression of each stabilized cytoplasmic membrane protein measured as defined in step (b) for each of the subpopulations of leukocytes and platelets present in the sample and identified as defined above.

2. The procedure of claim 1, wherein said sample in step (a) is a normal or pathologic sample obtained in vivo, stored or treated in vitro.

3. The procedure of claim 1, wherein more than one protease inhibitor is provided, each specific for a different cell membrane protease.

4. The procedure of claim 1, wherein said protease inhibitor is selected from the group consisting of amino acids, and peptides.

5. The procedure of claim 1, further comprising a step of identifying non-stabilized cytoplasmic membrane proteins, which are selected from the group consisting of oncoproteins and proteins associated with a cell cycle, apoptosis, cell activation and cell differentiation.

6. The procedure of claim 1, wherein after the step (a), said inhibitors are removed in order to explore kinetics of action of the proteases.

7. The procedure of claim 1, wherein the fluorescence emissions due to each fluorochrome-conjugated monoclonal antibody specific for a stabilized cytoplasmic membrane protein is evaluated by quantitative cytometric analytical techniques to quantify fluorescence.

8. The procedure of claim 1, wherein said incubation in said step (a) is performed in vivo prior to obtaining said sample.

* * * * *